United States Patent
Lukasik et al.

(10) Patent No.: US 6,699,434 B1
(45) Date of Patent: Mar. 2, 2004

(54) METERING VALVE TO DELIVER LIQUID

(75) Inventors: Robert G. Lukasik, Lake Elsinore, CA (US); Szu-Min Lin, Laguna Hills, CA (US)

(73) Assignee: Ethicon, Inc., Somerville, NJ (US)

( * ) Notice: Subject to any disclaimer, the term of this patent is extended or adjusted under 35 U.S.C. 154(b) by 587 days.

(21) Appl. No.: 09/658,312

(22) Filed: Sep. 8, 2000

(51) Int. Cl.⁷ .................................... A61L 2/00
(52) U.S. Cl. ................ 422/33; 137/625.46; 422/28; 422/29; 422/292; 422/295
(58) Field of Search ............... 422/28, 33, 29, 422/292, 295; 137/625.46

(56) References Cited

U.S. PATENT DOCUMENTS

| | | |
|---|---|---|
| 3,650,305 A | 3/1972 | Hendershot |
| 3,653,266 A | 4/1972 | Holmes |
| 3,680,736 A | 8/1972 | Viessmann |
| 4,643,876 A | 2/1987 | Jacobs et al. |
| 4,744,955 A | 5/1988 | Shapiro |
| 4,817,800 A | 4/1989 | Williams et al. |
| 4,821,929 A | 4/1989 | Srisathapat |
| 4,913,196 A | 4/1990 | Williams et al. |
| 4,938,262 A | 7/1990 | Williams et al. |
| 4,941,518 A | 7/1990 | Williams et al. |
| 5,348,711 A * | 9/1994 | Johnson et al. ............. 422/300 |
| 5,405,061 A | 4/1995 | Kügler |
| 5,527,507 A * | 6/1996 | Childers et al. .............. 422/28 |
| 5,882,611 A | 3/1999 | Williams et al. |
| 5,887,716 A | 3/1999 | Williams et al. |
| 6,273,134 B1 * | 8/2001 | Edwards et al. ....... 137/625.46 |

FOREIGN PATENT DOCUMENTS

| | | |
|---|---|---|
| EP | 0 266 517 A2 | 5/1988 |
| GB | 2 024 158 A | 1/1980 |
| GB | 2 322 431 A | 8/1998 |

OTHER PUBLICATIONS

European Search Report dated Jan. 25, 2002, regarding European Patent Application No. EP 01 30 7641.

* cited by examiner

Primary Examiner—Krisanne Thornton

(57) ABSTRACT

A metering valve for delivering liquids from a reservoir includes a rotatable valve plug having at least one well in the valve plug. The valve plug prevents direct communication across the valve. Rotating the valve plug transfers the liquid from the reservoir into the well on the valve plug. Rotating the valve plug further transfers the liquid in the well from the valve plug to the point of delivery. The rotation of the valve plug can be repeated to transfer more liquid. The metering valve can be used to deliver vaporizable germicides to a sterilization chamber. A single metering valve can be used to deliver varying amounts of vaporizable germicide to different sizes of sterilization chamber by rotating the valve plug an appropriate number of times. The valve plug can contain multiple wells to deliver large volumes of liquid quickly.

14 Claims, 8 Drawing Sheets

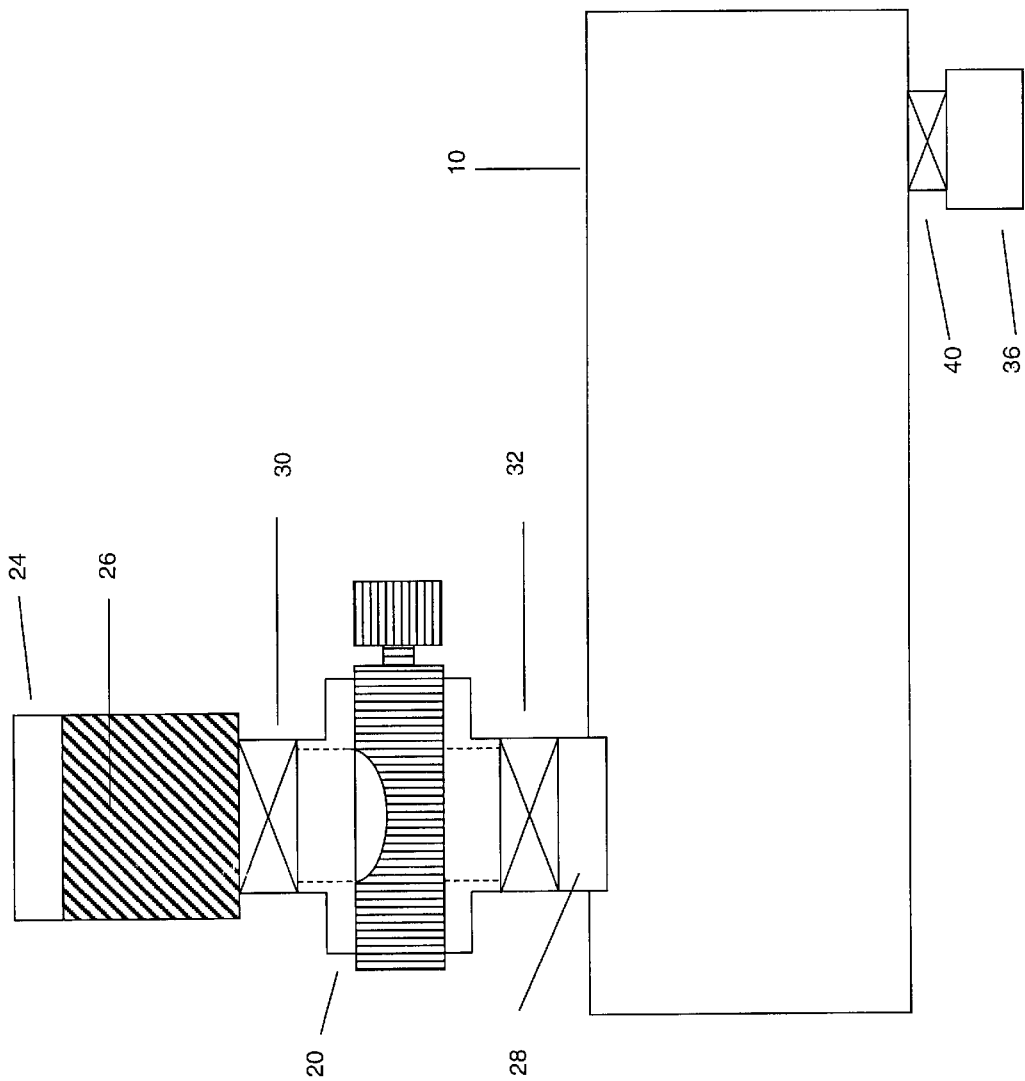

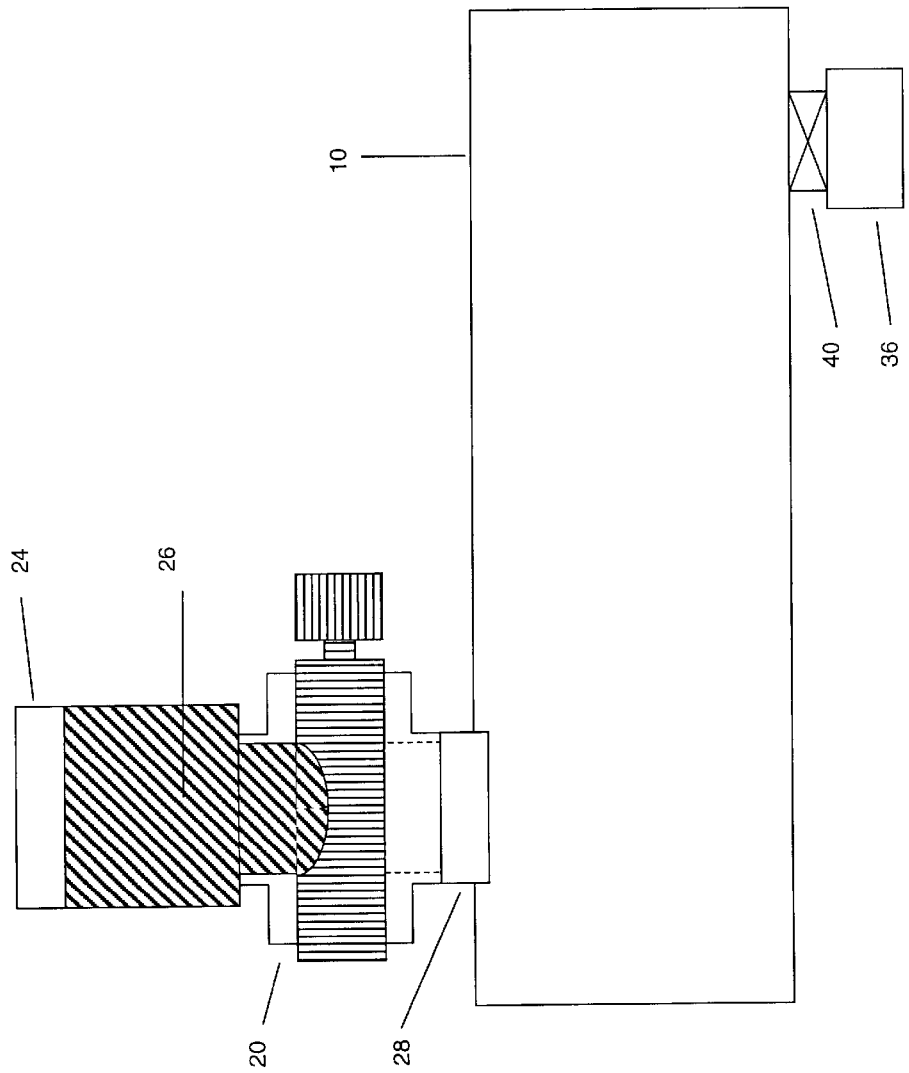

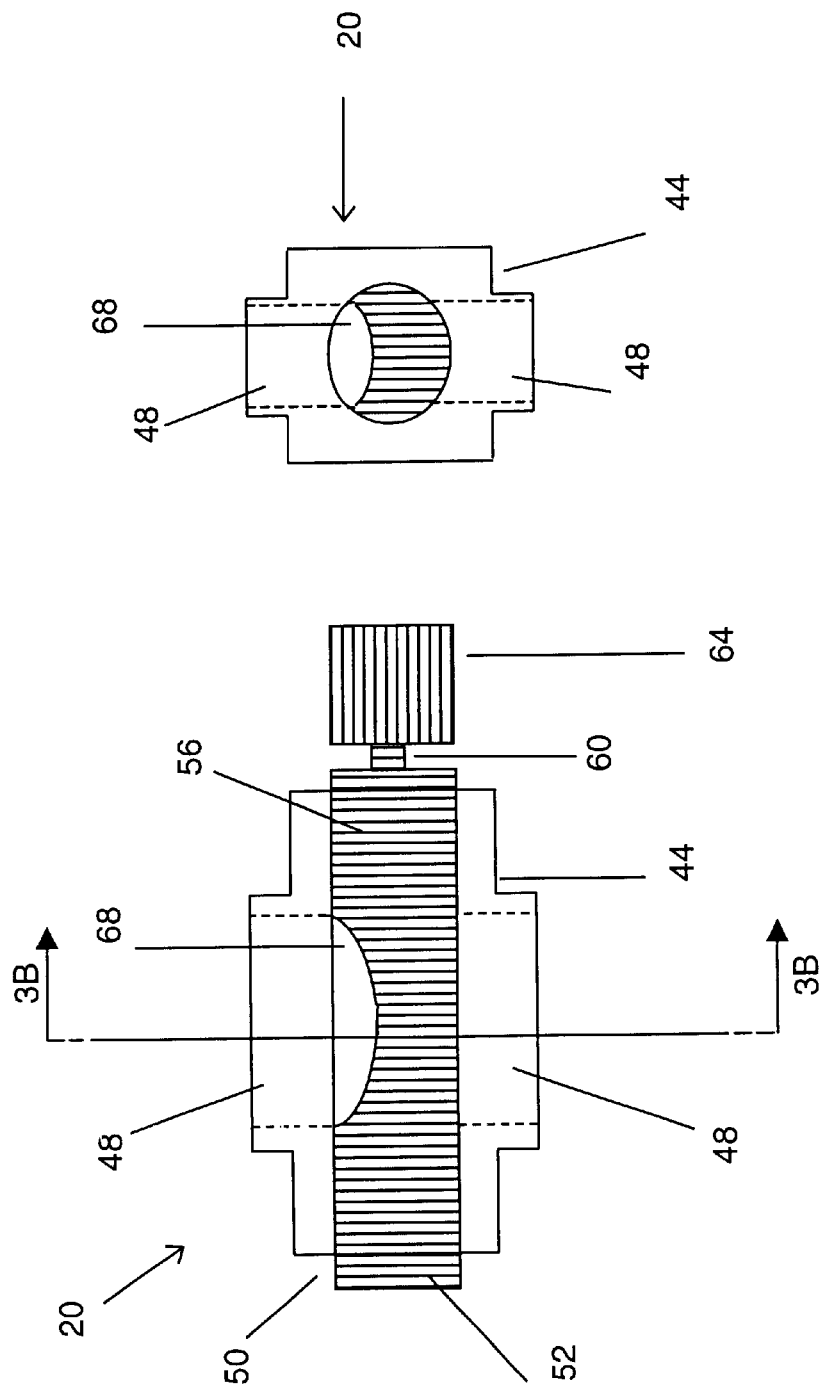

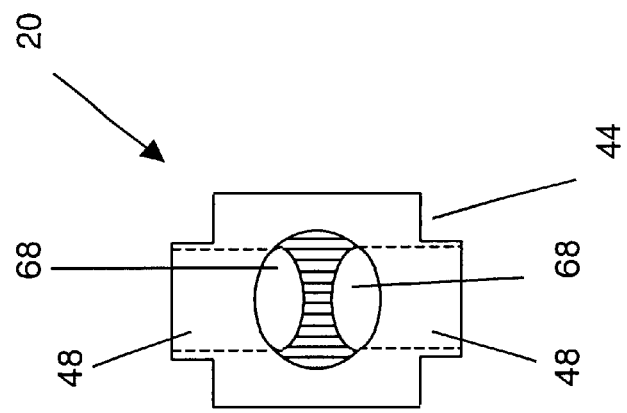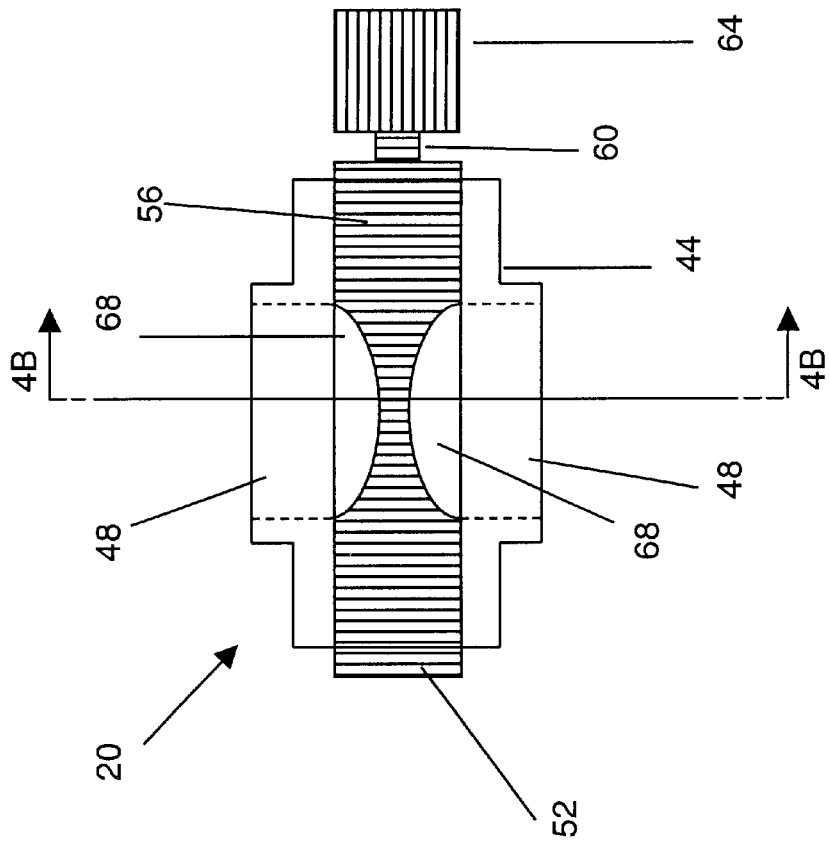

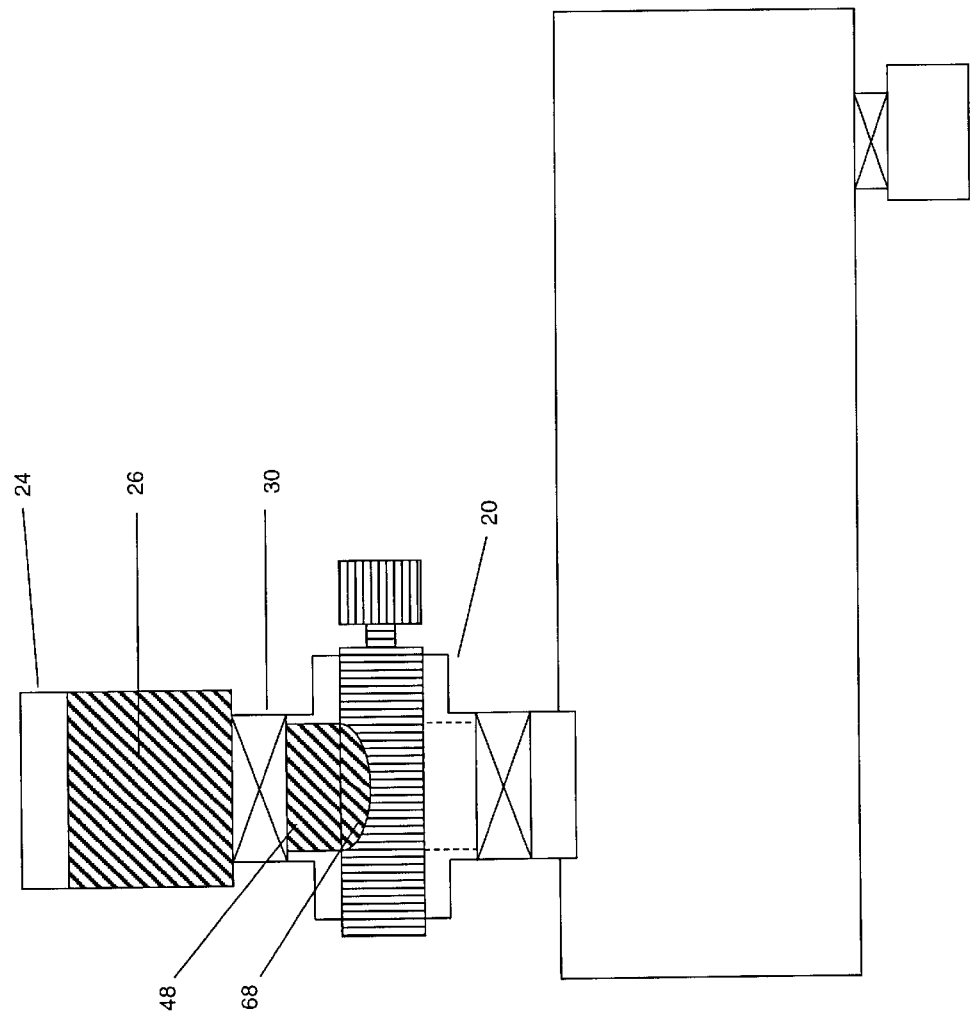

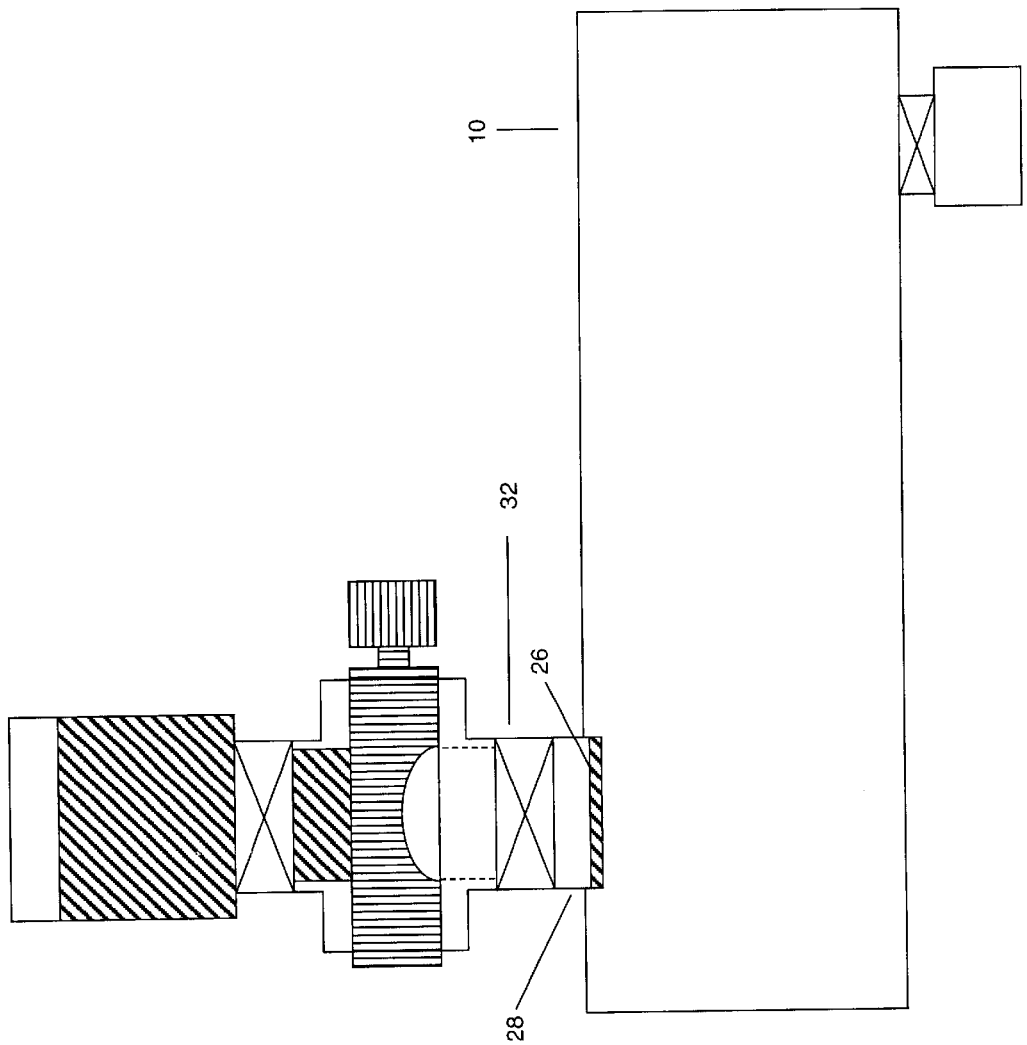

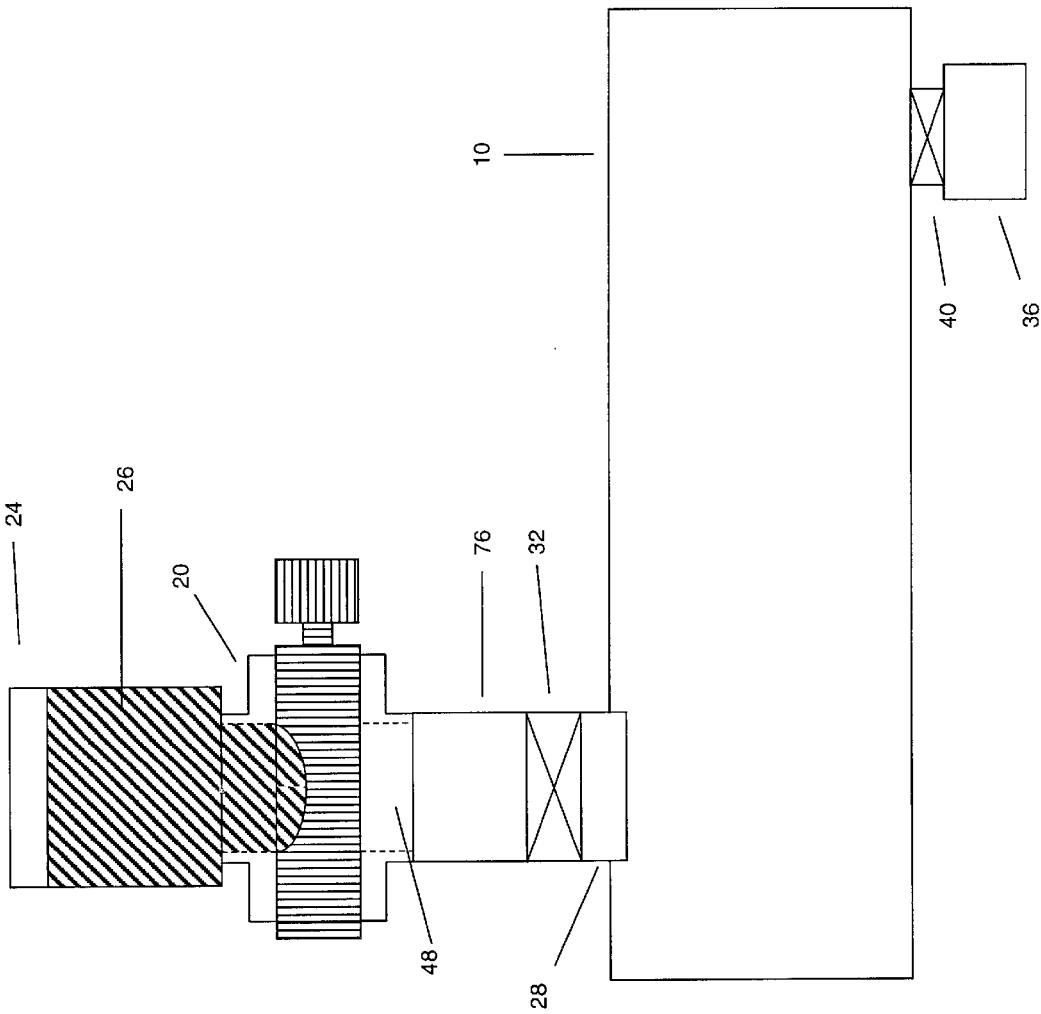

METERING VALVE TO DELIVER LIQUID

BACKGROUND OF THE INVENTION

1. Field of the Invention

This invention relates to a metering valve for delivering liquid vaporizable germicide to a sterilizer.

2. Description of the Related Art

Sterilization is used in a broad range of industrial and medical applications. Sterilization is the complete destruction or the irreversible inactivation of all the microorganisms in the system. Sterilization can be performed, for example, with heat or chemical treatment. Heat sterilization is normally done using steam. Some equipment cannot withstand the heat or the moisture of stem treatment. As a result, chemical sterilization is now commonly used.

Chemical sterilization can be done using alcohols, aldehydes such as formaldehyde, phenols, ozone, ethylene oxide, chlorine dioxide, or hydrogen peroxide. Hydrogen peroxide is commonly used for chemical sterilization.

U.S. Pat. No. 4,653,876, incorporated herein by reference, discloses an exemplary sterilization process in which a vaporizable germicide such as hydrogen peroxide is introduced into an evacuated sterilization chamber. The vaporizable germicide vaporizes and is allowed to disperse throughout the chamber and onto the items to be sterilized. After a period of time, electrical energy is applied to an electrode to form a plasma to complete the sterilization cycle.

The STERRAD® Sterilization System is an exemplary hydrogen peroxide sterilization system, commercially available from Advanced Sterilization Products, Irvine, Calif. Advanced Sterilization Products is a Division of Ethicon Endo-Surgery, Inc. The system employs an automated delivery system in which a measured amount of the liquid germicide, typically aqueous hydrogen peroxide, is delivered to the sterilization chamber. Measured portions of the liquid germicide are provided in rupturable cells within a liquid cassette housing. The cassette and the delivery system are fully described in the Williams et al. patents, U.S. Pat. No. 4,817,800, issued Apr. 4, 1989; U.S. Pat. No. 4,913,196, issued Apr. 3, 1990; U.S. Pat. No. 4,938,262, issued Jul. 3, 1990; and U.S. Pat. No. 4,941,518, issued Jul. 17, 1990, all of which are incorporated herein by reference.

Although the cassette and the delivery system work well, the delivery system is complex and expensive. There is a need for a delivery system which is simpler and less expensive than the cassette delivery system. Further, the volumes of vaporizable germicide which can be delivered to the sterilization chamber with the cassette delivery system are limited to incremental volumes of single cells on the cassette. For example, 1½ cells of hydrogen peroxide cannot easily be delivered with the cassette delivery system. Because the amount of hydrogen peroxide required for sterilization depends on the size of the sterilization chamber, the quantity of equipment in the chamber to be sterilized, the materials from which the equipment to be sterilized is made, and many other factors, there are times when it would be useful to be able to add small additional increments of hydrogen peroxide into the sterilization chamber rather than being limited to adding an entire cell of vaporizable germicide from a cassette.

There is a need for a simple, inexpensive system for metering vaporizable germicide into a sterilization chamber in which the amount of vaporizable germicide can be varied in small incremental increments. There is a need for a simple vaporizable germicide delivery system which can deliver a wide range of volumes of vaporizable germicide to match the needs of various sizes of sterilization chambers.

SUMMARY OF THE INVENTION

One aspect of the invention involves a metering valve for delivering liquid to system. The metering valve includes a body having at least a first and a second orifice; and a rotatable valve plug located in the body, where the rotatable valve plug prevents direct fluid communication between the first orifice and the second orifice. The valve plug includes at least one well, where the well comes into fluid communication separately with the first orifice and the second orifice as the valve plug is rotated.

Advantageously, the orifices are located approximately 180 degrees apart in the valve body. The valve plug can be rotated manually or with a motor. In an embodiment, the valve plug includes at least two wells. The two wells may have different sizes or shapes. Preferably, the first orifice is never brought into direct fluid communication with the second orifice as said rotatable valve plug is rotated.

Another aspect of the invention involves a system for sterilizing equipment, where the system includes a metering valve. The metering valve includes a body with at least two orifices and a rotatable valve plug located in the body. The valve plug prevents direct fluid communication between the two orifices. The valve plug includes at least one well. The well comes into fluid communication separately with the two or more orifices as the valve plug is rotated. The system also includes a reservoir connected to a first orifice on the metering valve. The reservoir contains vaporizable germicide. The system also includes a sterilization chamber, where the sterilization chamber receives vaporizable germicide from a second orifice on the metering valve.

Preferably, the system also includes a vaporizer connected to the second orifice on the metering valve. The vaporizer is in fluid communication with the sterilization chamber. Advantageously, the system also includes a vacuum pump connected to the sterilization chamber. The system may include a source of plasma. An accumulator may be located between the second orifice on the metering valve and the sterilization chamber. An on/off valve may optionally be located between the metering valve and the sterilization chamber and/or between the metering valve and the reservoir. Advantageously, the vaporizable germicide is hydrogen peroxide.

Another aspect of the invention involves a method for sterilizing an article in a chamber. The method includes providing a source of vaporizable germicide, a chamber, and a metering valve for delivering germicide to the chamber. The metering valve includes a body having at least two orifices and a rotatable valve plug located in the body. The valve plug prevents direct fluid communication between the two orifices. There is at least one well in the valve plug. The well comes into fluid communication separately with the orifices as the valve plug is rotated. The metering valve is in fluid communication with the chamber and the source of vaporizable germicide. Rotating the valve plug transfers vaporizable germicide from the source of germicide into the well and from the well into the chamber.

Advantageously, the method also includes reducing the pressure in the chamber. Preferably, reducing the pressure vaporizes the vaporizable germicide, sterilizing the article in the chamber. In a preferred embodiment, the vaporizable germicide is accumulated in an accumulator located between the metering valve and the chamber. The article may be contacted with plasma. Preferably, the vaporizable germicide is hydrogen peroxide. The method may also include opening or closing a valve between the metering valve and the source of vaporizable germicide or between the metering valve and the chamber.

BRIEF DESCRIPTION OF THE DRAWINGS

FIG. 1 is a schematic drawing showing a sterilization system and a cross section of a metering valve according to an embodiment of the invention;

FIG. 2 is a schematic drawing of the sterilization system and metering valve of FIG. 1, where there are no optional on/off valves between the metering valve and the reservoir or the vaporizer;

FIG. 3A shows a schematic cross sectional side view of a metering valve according to an embodiment of the invention, where there is one well in the valve plug;

FIG. 3B shows a schematic cross sectional view of the metering valve of FIG. 3A along the 3B—3B axis of FIG. 3A;

FIG. 4A shows a schematic cross sectional side view of a metering valve according to an embodiment of the invention, where there are two wells in the valve plug;

FIG. 4B shows a schematic cross section of the metering valve of FIG. 4A along the 4B—4B axis of FIG. 4A;

FIG. 5 shows a schematic drawing of the sterilization system and metering valve of FIG. 1 after vaporizable germicide has been admitted into the orifice on the top of the metering valve of FIG. 1;

FIG. 7 shows a schematic drawing of the sterilization system and metering valve of FIG. 6 after the on/off valve above the vaporizer has been opened, allowing liquid vaporizable germicide to be transferred from the top of the on/off valve into the vaporizer; and FIG. 8 is a schematic drawing showing a sterilization system, a cross section of the metering valve of FIG. 3A, and an accumulator above the vaporizer.

DETAILED DESCRIPTION OF THE PREFERRED EMBODIMENT

Figure 6:
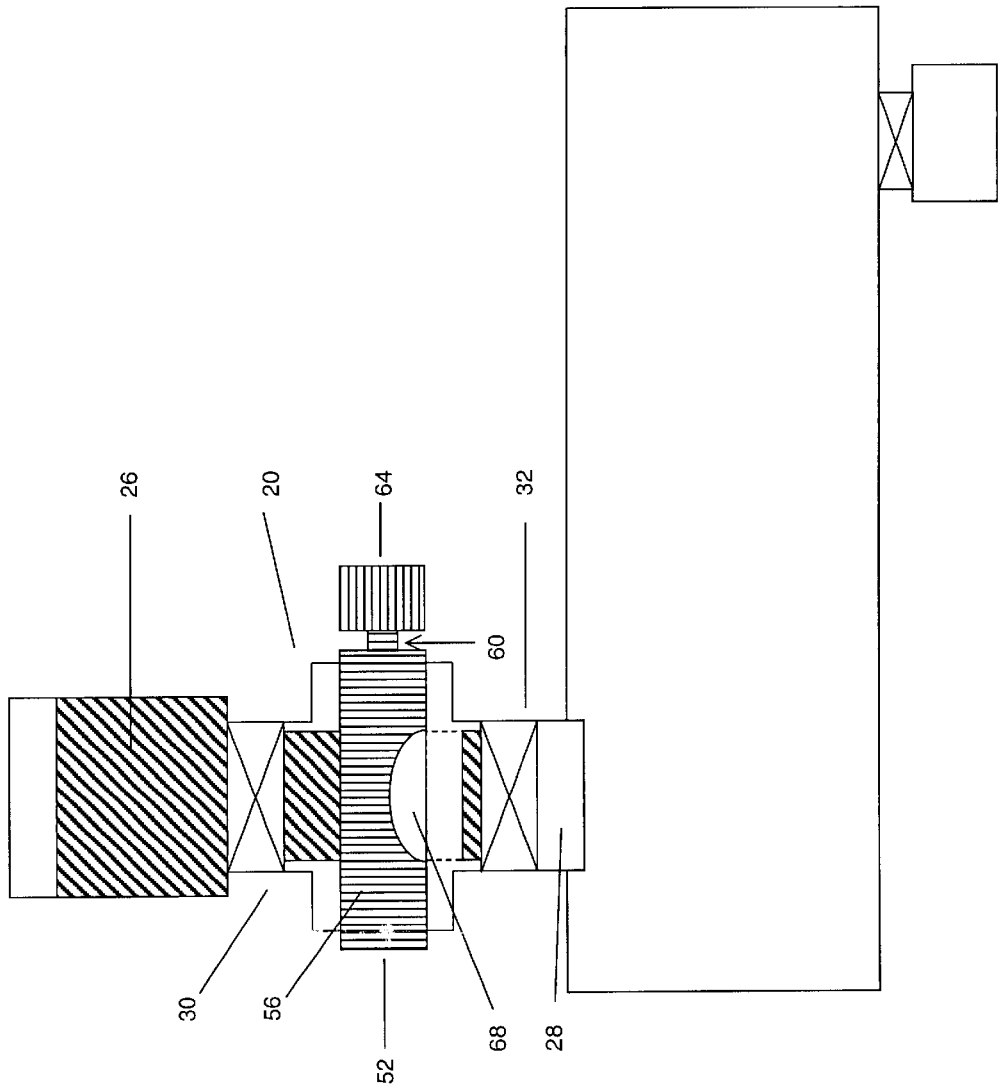
FIG. 6 shows a schematic drawing of the sterilization system and metering valve of FIG. 5 after the handle of the metering valve has been turned, transferring the vaporizable germicide in the well of the metering valve to the top of the on/off valve above the vaporizer.

FIG. 1 shows a schematic diagram of a sterilization chamber 10 with a metering valve 20 according to an embodiment of the invention. The sterilization chamber 10 and its components and methods of use are described in detail in U.S. Pat. No. 4,756,882, issued Jul. 12, 1988; U.S. Pat. No. 5,656,238, issued Aug. 12, 1997; and U.S. Pat. No. 6,060,019, issued May 9, 2000, all of which are incorporated herein by reference. The metering valve 20 is mounted below a reservoir 24 which contains vaporizable germicide 26 and above a vaporizer 28 which is located above and which is fluidly attached to the sterilization chamber 10. Optional on/off valves 30 and 32 are located between the reservoir 24 and the metering valve 20 and/or between the metering valve 20 and the vaporizer 28. A vacuum pump 36 and a shutoff valve 40 are fluidly connected with the sterilization chamber 10.

Although the metering valve 20 is described in the context of a metering valve for delivering vaporizable germicide to a sterilization chamber 10, it is to be understood that the application of the metering valve 20 to sterilization is illustrative only. The metering valve 20 of the present invention has many uses, and the example of delivering vaporizable germicide to a sterilization chamber 10 with the metering valve 20 is not meant to be limiting. The term germicide is meant to include either germicide or disinfectant. Further, the metering valve 20 can be used to deliver liquids, solids, and slurries of solids in one or more liquids.

FIG. 2 shows a schematic diagram of a sterilization chamber 10 and metering valve 20 in which there are no optional on/off valves 30 and 32 located between the reservoir 24 and the metering valve 20 and between the metering valve 20 and the vaporizer 28.

FIGS. 3A and 3B show two views of a metering valve 20 according to an embodiment of the invention. The metering valve 20 has a generally rectangular shaped body 44 with open orifices 48 at a top and a bottom of the body 44. As seen in cross-sectional side view FIG. 3A and cross sectional end view FIG. 3B, the two orifices 48 form an open tube extending through the body 44 of the metering valve 20. An roughly cylindrical valve plug channel 50 extends through the body 44 perpendicular to the first open tube formed by the two orifices 48. The valve plug channel 50 forms a second tube in the body 44 perpendicular to the first open tube formed by the two orifices 48. The valve plug channel 50 in FIGS. 3A and 3B contains a valve plug 52.

Although the body 44 shown in FIGS. 3A and 3B has a roughly rectangular shape, the body 44 may have other shapes such as a cylindrical shape or other appropriate shapes.

The valve plug 52 has a generally cylindrical center section, the barrel 56, with a rod-like valve stem 60 extending from an end of the barrel 56. A handle 64 is connected to the valve stem 60. Alternatively, a motor (not shown) can be connected to the valve stem 60 in place of, or in addition to, the handle 64.

The tube formed by the two orifices 48 is plugged by the barrel 56 of the valve plug 52. The barrel 56 of the valve plug 52 prevents fluid communication between the two orifices 48 on the body 44 of the metering valve 20. The ends of the barrel 56 and the valve stems 60 form a seal with the body 44 of the metering valve 20. The valve plug 52 may be rotated in the body 44 of the metering valve 20 by turning the handle 60 or motor (not shown). The valve plug 52 is held in place in the body 44 of the metering valve 20.

In other embodiments, the valve plug 52 can have other shapes. For example, in an embodiment, the valve plug 52 has the shape of a tapered cylinder rather than a simple cylinder, as in the embodiment shown in FIGS. 3A and 3B. What is important that the valve plug 52 block the fluid communication between the two orifices 48 and that the valve plug 52 provide a seal with the body 44 of the metering valve 20.

There is a well 68 having a roughly semicircular shaped cross section in the barrel 56 of the valve plug 52 in the embodiment of the metering valve 20 shown in FIGS. 3A and 3B. The well 68 extends through only part of the barrel 56. In other embodiments, the well 64 can have other cross-sectional shapes such as a rectangular shape, a V-shape, or a trapezoid shape. As seen in FIG. 3B, the well 68 is located under one of the orifices 48 when the valve plug 52 is placed in the body 44 of the metering valve 20 and when the well 68 is oriented so that the well 68 is oriented with an open side of the well 68 directed upward. In other embodiments, the well 68 is not centered under the orifice 48 but is located asymmetrically below the orifice 48. At least a portion of the well 68 is in fluid communication with the orifice 48 when the open side of the well 68 is directed toward the orifice 48. Unlike a conventional valve, the orifices 48 of the metering valve 20 of FIGS. 3A and 3B are never in fluid communication with each other, no matter how the valve plug 52 is rotated.

The size of the well 68 may depend on the size of the sterilization chamber 10. In an exemplary embodiment, the well 68 has a size which is appropriate for holding an amount of vaporizable germicide 26 which is appropriate for the smallest sterilization chamber 10 to which the metering valve 10 is to be applied. In an embodiment appropriate for the STERRAD® sterilizer, the well 68 has a volume of approximately 1 milliliter. In embodiments appropriate for other sterilization chambers 10, the well 68 has a volume larger or smaller than 1 milliliter.

FIGS. 4A and 4B show an alternative embodiment of the metering valve 20 in which there are two wells 68 in the barrel 56 of the valve plug 52. The wells 68 are positioned on the valve plug 52 so that at least a portion of each of the wells 68 is in fluid communication with an orifice 48 when the orifice 48 is aligned with the well 68. In the embodiment of the metering valve 20 shown in FIGS. 4A and 4B, the two wells 68 are located on opposite sides of the valve plug 52. In the embodiment of FIGS. 4A and 4B, when the well 68 at the top of the valve plug 52 is in fluid communication with the orifice 48 at the top of the metering valve 20, the well 68 at the bottom of the valve plug 52 is in fluid communication with the orifice 48 at the bottom of the metering valve 20. The two wells 68 are never in fluid communication with each other, no matter how the valve plug 52 is rotated.

The two wells 68 of the metering valve 20 of FIGS. 4A and 4B are approximately 180° apart from each another. In other embodiments of the metering valve 20 with two wells 68, the wells 68 are at not 180° apart from each other, and only one of the wells 68 may be in fluid communication with an orifice 48 at any one time. In this embodiment, rotating the valve plug 52 causes the other well 68 to be in fluid communication with the orifice 48. In other embodiments, there may be three or more wells 68 in the valve plug 52. In all of the embodiments of the valve plug 20, the wells 68 are not in direct fluid communication with each other, and the orifices 48 are not in direct fluid communication with each other. In the embodiments of the metering valve 20 with at least two wells 68, the wells 68 can have different sizes or shapes.

The metering valve 20 can be made from a wide range of materials, including metal, glass, or plastic. Suitable metals include steel or aluminum. Stainless steel is an exemplary metal for forming the metering valve 20. TEFLON™ is an exemplary material for forming the metering valve 20. TEFLON™ is the tradename for polytetrafluoroethylene.

The seal between the valve plug 52 and the body 44 of the metering valve 20 can be achieved in several ways, depending on the material from which the metering valve is fabricated. If the valve plug 52 and the body 44 of the metering valve are both made of TEFLON™, the valve plug 52 and the body 44 can be fabricated so that the contact between the TEFLON™ valve plug 52 and the TEFLON™ body 44 forms a seal.

In another embodiment, the valve plug 52 is made of TEFLON™, and the body 44 is made of metal. If the valve plug 52 and the body 44 are properly fabricated, the contact between the TEFLON™ valve plug 52 and the metal body 44 forms a seal. In another embodiment, the valve plug 52 is made of TEFLON™, and the body 44 is made of glass. In another embodiment, both the valve plug 52 and the body 44 are made of metal. O-rings or packing can be placed on the valve plug 52 to form a seal between the valve plug 52 and the body 44.

If O-rings or packing are used in the metering valve 20, the O-rings or packing are preferably formed of a material which is resistant to the vaporizable germicide 26 which is used. VITON™ is an exemplary material for forming the O-rings or packing. TEFLON™ or silicone may also be used to form the O-rings or packing.

Returning to FIG. 1, vaporizable germicide 26 is placed in the reservoir 24 above the optional on/off valve 30. The vaporizable germicide 26 can be any liquid vaporizable germicide including hydrogen peroxide, peracetic acid, chlorine dioxide, ozone, or formaldehyde. In an exemplary embodiment, the vaporizable germicide 26 comprises aqueous hydrogen peroxide. In a preferred embodiment, the vaporizable germicide 26 is approximately 59 wt % aqueous hydrogen peroxide. The shutoff valve 40 between the vacuum pump 36 and the sterilization chamber 10 is opened, and the sterilization chamber 10 is evacuated to a pressure of less than 50 torr, more preferably less than 10 torr, and most preferably less than 1 torr with the vacuum pump 36. After the sterilization chamber 10 is evacuated, shutoff valve 40 between the vacuum pump 36 and the sterilization chamber 10 may be closed to isolate the sterilization chamber 10 from the vacuum pump 36. In an alternative embodiment which will be described in more detail later, the shutoff valve 40 between the vacuum pump 36 and the sterilization chamber 10 is left open.

In FIG. 5, the on/off valve 30 between the reservoir 24 and the metering valve 20 has been opened, allowing vaporizable germicide 26 to enter the orifice 48 and the well 68 on the metering valve 20.

In FIG. 6, the handle 64 or motor on the metering valve 20 has been rotated, rotating the valve plug 52. As the valve plug 52 rotates, the vaporizable germicide 26 in the well 68 in the valve plug 52 of the metering valve 20 falls out of the well 68 onto the top of on/off valve 32.

In FIG. 7, on/off valve 32 has been opened, allowing the vaporizable germicide 26 which was on top of the on/off valve 32 in FIG. 6 to enter the vaporizer 28. The vaporizer 28 is fluidly connected to the interior of the sterilization chamber 10. The vaporizer is maintained at a temperature of 60 to 70° C. As the vaporizable germicide 26 enters the hot vaporizer 28, the vaporizable germicide 26 vaporizes, and the germicide vapor enters the sterilization chamber 10. The germicide vapor contacts the equipment to be sterilized (not shown) in the sterilization chamber 10, sterilizing the equipment. Optionally, plasma is introduced into or is generated in the sterilization chamber 10 to enhance the sterilization by the germicide vapor or to remove the germicide residual.

Returning to FIG. 6, the handle 64 or the motor on the metering valve 20 can optionally be rotated more than one time. Each time the handle 64 is rotated, a volume of vaporizable germicide 26 equal to the volume of the well 68 is delivered to the top of the on/off valve 32. When the desired amount of vaporizable germicide 26 has been delivered to the top of the on/off valve 32, the on/off valve 32 is opened, allowing the vaporizable germicide 26 to enter the vaporizer 28. By knowing the volume of the well 68 and the number of times the handle 64 or motor has been rotated, the amount of vaporizable germicide 26 which has been delivered to the vaporizer 28 can be determined.

In the embodiment of the metering valve 20 shown in FIGS. 4A and 4B, there are two wells 68 on the valve plug 52. Each rotation of the handle 64 on the metering valve 20 delivers a volume of vaporizable germicide 26 equal to the volume of the two wells 68, rather than the volume of a single well 68. The embodiment of the metering valve 20 shown in FIGS. 3A and 3B thus delivers twice as much vaporizable germicide 26 for each rotation of the valve plug 52 as the embodiment of the metering valve 20 shown in FIGS. 3A and 3B. Vaporizable germicide 26 can enter the well 68 at the top of the metering valve 20 from the orifice 48 at the top of the metering valve 20 at the same time that vaporizable germicide 26 exits the well 68 at the bottom of the metering valve 20.

In an alternative embodiment of the apparatus such as shown in FIG. 2, there is no on/off valve 32 below the metering valve. In the alternative embodiment, the vaporizable germicide 26 enters the vaporizer 28 directly after leaving the well 68. The handle 64 on the metering valve 20 can be rotated multiple times to add more vaporizable germicide 26. In the alternative embodiment, the vaporizable germicide 26 enters the vaporizer. 28 incrementally each time the handle 64 is rotated rather than at one time when the on/off valve 32 is opened.

FIG. 8 shows another embodiment of the apparatus suitable for delivering larger volumes of vaporizable germicide 26 than the embodiment of the apparatus shown in FIG. 1. In the embodiment of the apparatus shown in FIG. 8, there is no on/off valve 30 between the reservoir 24 and the metering valve 20. In another embodiment, there is an on/off valve 30 between the reservoir 24 and the metering valve 20. An accumulator 76 is located between the metering valve 20 and the on/off valve 32 located above the vaporizer 28. The volume of the accumulator 76 is larger than the volume of the orifice 48 at the bottom of the metering valve 20. By including the accumulator 76 in the apparatus, a larger volume of vaporizable germicide 26 can be placed on top of the on/off valve 32 above the vaporizer 28 than in the embodiment of the apparatus shown in FIG. 1, where the volume of vaporizable germicide 26 on top of the on/off valve 32 is limited to the volume of the orifice 48 at the bottom of the metering valve 20. After the desired volume of vaporizable germicide 26 has been delivered to the accumulator 76, the on/off valve 32 is opened, delivering the vaporizable germicide 26 to the vaporizer 28.

Accumulating larger volumes of vaporizable germicide 26 in the accumulator 76 of FIG. 8 has advantages over simply allowing the vaporizable germicide 26 to enter the vaporizer 28 directly, when the vaporizable germicide 26 comprises hydrogen peroxide and water. Water has a higher vapor pressure than hydrogen peroxide. If the valve 40 between the sterilization chamber 10 and the vacuum pump 36 is left open when the on/off valve 32 is opened, allowing the vaporizable germicide 26 to enter the vaporizer 28, water is preferentially removed from the sterilization chamber 10 into the vacuum pump 36, because the water has a higher vapor pressure than hydrogen peroxide, and the vapor in the sterilization chamber 10 is enriched in water vapor compared to the vaporizable germicide 26 in the accumulator 76. Removing water from the aqueous hydrogen peroxide in the accumulator 76 by removing the water vapor in the sterilization chamber 10 concentrates the hydrogen peroxide.

After a certain period of time apparent to one of ordinary skill in the art, the valve 40 leading to the vacuum pump 36 is closed, and the concentrated hydrogen peroxide is allowed to vaporize from the vaporizer 28 into the sterilization chamber 10. The concentrated hydrogen peroxide in the vaporizer 28 vaporizes to produce a vapor which has a higher concentration of hydrogen peroxide than if water had not been removed from the aqueous hydrogen peroxide in the accumulator 76 by preferential vaporization. The concentrated hydrogen peroxide vapor is more effective at sterilization than hydrogen peroxide vapor produced from a less concentrated solution of aqueous hydrogen peroxide.

Allowing the aqueous hydrogen peroxide vaporizable germicide to accumulate in the accumulator 76 is therefore a preferred embodiment. The aqueous hydrogen peroxide in the accumulator 76 can be concentrated by removing water vapor from the sterilization chamber 10 through the valve 40 and the vacuum pump 36, improving the effectiveness of the sterilization.

The metering valve 20 of the present invention is an apparatus which provides a way to readily deliver a wide range of volumes of vaporizable germicide 26 to the sterilization chamber 10 without having to change the size of the delivery system, depending on the size of the sterilization chamber 10. The metering valve 20 of the present invention is a simple device which is inexpensive to manufacture and easy to use. The volume of vaporizable germicide 26 which is delivered to the vaporizer 28 can be controlled by rotating the handle 64 or motor (not shown) on the metering valve 20. Each rotation of the handle 64 delivers a volume of vaporizable germicide 26 equal to the volume of the well 68 on the valve plug 52. The incremental volumes of vaporizable germicide 26 to be delivered to the sterilization chamber 10 are not limited to the volume of a cell on a sterilization cassette. If multiple wells 68 are present on the valve plug 52, each rotation of the handle 64 delivers a volume of vaporizable germicide 26 equal to the volume of each well 68 times the number of wells 68 on the valve plug 52.

In some embodiments, more than one metering valve 20 may be located in parallel between the reservoir 24 and the vaporizer 28. The metering valves 20 can have wells 68 of differing sizes or shapes. In this embodiment, the metering valve 20 can be selected for use which has a well 68 with a size which is optimal for the size of the sterilization chamber 10.

Various modifications and alterations of this invention will be apparent to those skilled in the art without departing from the scope and spirit of this invention. It should be understood that the invention is not limited to the embodiments disclosed therein, and that the claims should be interpreted as broadly as the prior art allows.

What is claimed is:

1. A system for sterilizing equipment, said system comprising:

a metering valve, said metering valve comprising:

a body comprising at least a first and a second orifice; and a rotatable valve plug located in said body, wherein said valve plug prevents direct fluid communication between said first orifice and said second orifice, said valve plug comprising at least one well, wherein said at least one well comes into fluid communication separately with said first orifice and said second orifice as said rotatable valve plug is rotated;

a reservoir connected to said first orifice of said metering valve, wherein said reservoir contains vaporizable germicide;

an accumulator connected to said second orifice, wherein said accumulator receives said vaporizable germicide from said second orifice of said metering valve; and a sterilization chamber connected to said accumulator, wherein said sterilization chamber receives said vaporizable germicide from said accumulator.

2. The system of claim 1, further comprising a vaporizer, wherein said vaporizer is in fluid communication with said accumulator and is in fluid communication with said sterilization chamber.

3. The system of claim 1, further comprising a vacuum pump connected to said sterilization chamber.

4. The system of claim 1, further comprising a source of plasma.

5. The system of claim 1, further comprising an on/off valve located between said metering valve and said sterilization chamber and/or an on/off valve located between said metering valve and said reservoir.

6. The system of claim 1, wherein said vaporizable germicide comprises hydrogen peroxide.

7. A method for sterilizing an article in a chamber, said method comprising:

providing a source of vaporizable germicide;

providing a chamber;

providing a metering valve for delivering vaporizable germicide from said source of vaporizable germicide to said chamber, said metering valve comprising:

a body comprising at least a first and a second orifice; and a rotatable valve plug located in said body, wherein said rotatable valve plug prevents direct fluid communication between said first orifice and said second orifice, said valve plug comprising at least one well, wherein said first orifice and said second orifice as said rotatable valve plug is rotated and wherein said metering valve is in fluid communication with said chamber and said source of vaporizing germicide;

rotating said rotatable valve plug, thereby transferring said vaporizable germicide from said source of vaporizable germicide into said at least one well;

accumulating the vaporizable germicide from the at least one well in an accumulator located between the metering valve and the chamber; and transferring the vaporizable germicide from the accumulator into the chamber.

8. The method of claim 7, further comprising reducing the pressure in said chamber.

9. The method of claim 8, further comprising vaporizing said vaporizable germicide, thereby sterilizing said article in said chamber.

10. The method of claim 7, further comprising contacting said article with plasma.

11. The method of claim 7, wherein said vaporizable germicide comprises hydrogen peroxide.

12. The method of claim 8, further comprising opening or closing a valve between said metering valve and said source of vaporizable germicide or between said metering valve and said chamber.

13. The method of claim 7, wherein rotating said rotatable valve plug comprises rotating the rotatable valve plug multiple times.

14. The method of claim 7, further comprising repeating said rotating said rotatable valve plug and said accumulating the vaporizable germicide and said transferring the vaporizable germicide, thereby repeating the transfer of vaporizable germicide from the source into the chamber.

* * * * *